US006952652B2

(12) United States Patent
Butters

(10) Patent No.: US 6,952,652 B2
(45) Date of Patent: Oct. 4, 2005

(54) SYSTEM AND METHOD FOR SAMPLE DETECTION BASED ON LOW-FREQUENCY SPECTRAL COMPONENTS

(75) Inventor: Bennett M. Butters, Lacey, WA (US)

(73) Assignee: WavBank, Inc., Del Mar, CA (US)

( * ) Notice: Subject to any disclaimer, the term of this patent is extended or adjusted under 35 U.S.C. 154(b) by 52 days.

(21) Appl. No.: 10/805,066

(22) Filed: Mar. 19, 2004

(65) Prior Publication Data

US 2004/0174154 A1 Sep. 9, 2004

Related U.S. Application Data

(63) Continuation of application No. PCT/US03/11834, filed on Apr. 18, 2003.
(60) Provisional application No. 60/433,361, filed on Dec. 12, 2002, provisional application No. 60/374,941, filed on Apr. 19, 2002, and provisional application No. 60/374,043, filed on Apr. 19, 2002.

(51) Int. Cl.[7] .......................... G01N 31/00; G06F 19/00
(52) U.S. Cl. ........................... 702/27; 702/30; 702/190; 324/717
(58) Field of Search ................................ 324/204, 232, 324/750, 654, 717, 76.12, 76.29, 76.45; 702/35, 38, 27, 30, 189–191, 195, 197; 250/281

(56) References Cited

U.S. PATENT DOCUMENTS

| 4,095,168 A |   | 6/1978  | Hlavka            |         |
|-------------|---|---------|-------------------|---------|
| 4,365,303 A | * | 12/1982 | Hannah et al.     | 702/28  |
| 4,682,027 A | * | 7/1987  | Wells             | 250/291 |
| 4,692,685 A |   | 9/1987  | Blaze             |         |
| 4,751,515 A |   | 6/1988  | Corum             |         |

(Continued)

FOREIGN PATENT DOCUMENTS

| WO | WO 87/02981 A1 | 5/1987 |
|----|----------------|--------|
| WO | WO 91/13611 A1 | 9/1991 |
| WO | WO 91/14181 A1 | 9/1991 |

(Continued)

OTHER PUBLICATIONS

U.S. Appl. No. 10/923,545, Butters et al.
Cooley, J. et al., "An Algorithm for the Machine Calculation of Complex Fourier Series", Mathematics of Computation, Apr. 1965, pp. 297–301, vol. 19, No. 90, American Mathematical Society, Providence.

(Continued)

*Primary Examiner*—Patrick Assouad
*Assistant Examiner*—Paul Kim
(74) *Attorney, Agent, or Firm*—Perkins Coie LLP

(57) ABSTRACT

Method and apparatus for detecting a selected material in a sample are disclosed. In the method, the sample is placed adjacent a detector coil, for generating an electromagnetic time-domain signal composed of sample source radiation. The signal is first conditioned to convert the signal to an amplified conditioned signal from which frequency components above a selected frequency have been removed, then filtered to selectively pass low-frequency spectral components that are (i) in a frequency range between dc and 50 khz, and (ii) characteristic of the selected material. The filtered signal is cross-correlated with a data set of low-frequency spectral components that are (i) in a frequency range between dc and 50 khz, and (ii) characteristic of a selected material, to produce a frequency-domain spectrum in the frequency range within DC to 50 khz. This spectrum is then used to determine whether the frequency-domain spectrum contains one or more low-frequency signal components that are characteristic of the selected material, and diagnostic of the presence or absence of such material in the sample.

21 Claims, 10 Drawing Sheets

U.S. PATENT DOCUMENTS

| | | | |
|---|---|---|---|
| 4,822,169 A | | 4/1989 | Distl et al. |
| 5,254,950 A | | 10/1993 | Fan et al. |
| 5,343,147 A | | 8/1994 | Sager et al. |
| 5,446,681 A | * | 8/1995 | Gethner et al. ............... 702/27 |
| 5,458,142 A | | 10/1995 | Farmer et al. |
| 5,465,049 A | | 11/1995 | Matsuura et al. |
| 5,508,203 A | | 4/1996 | Fuller et al. |
| 5,541,413 A | | 7/1996 | Pearson et al. |
| 5,574,369 A | | 11/1996 | Hibbs |
| 5,583,432 A | * | 12/1996 | Barnes ...................... 324/204 |
| 5,656,937 A | | 8/1997 | Cantor |
| 5,734,353 A | | 3/1998 | Van Voorhies |
| 5,752,514 A | | 5/1998 | Okamura et al. |
| 5,789,961 A | | 8/1998 | Bulsara et al. |
| 5,952,978 A | | 9/1999 | Van Voorhies |
| 5,955,400 A | | 9/1999 | Yokosawa et al. |
| 5,959,548 A | | 9/1999 | Smith |
| 6,020,782 A | | 2/2000 | Albert et al. |
| 6,028,558 A | | 2/2000 | Van Voorhies |
| 6,136,541 A | | 10/2000 | Gulati |
| 6,142,681 A | | 11/2000 | Gulati |
| 6,159,444 A | | 12/2000 | Schlenga et al. |
| 6,196,057 B1 | | 3/2001 | Discenzo |
| 6,204,821 B1 | | 3/2001 | Van Voorhies |
| 6,285,249 B1 | | 9/2001 | Bulsara et al. |
| 6,320,369 B1 | | 11/2001 | Hidaka et al. |
| 6,323,632 B1 | | 11/2001 | Husher et al. |
| 6,541,978 B1 | | 4/2003 | Benveniste et al. |
| 6,724,188 B2 | | 4/2004 | Butters et al. |
| 2003/0016010 A1 | | 1/2003 | Kandori et al. |
| 2004/0027125 A1 | | 2/2004 | Clarke et al. |
| 2004/0183530 A1 | | 9/2004 | Butters et al. |

FOREIGN PATENT DOCUMENTS

| | | |
|---|---|---|
| WO | WO 94/17406 A1 | 8/1994 |
| WO | WO 99/54731 A1 | 10/1999 |
| WO | WO 00/01412 A1 | 1/2000 |
| WO | WO 00/17637 A1 | 3/2000 |
| WO | WO 00/17638 A1 | 3/2000 |
| WO | WO 03/83439 A2 | 10/2003 |

OTHER PUBLICATIONS

Aissa et al., "Transatlantic Transfer of Digitized Antigen Signal by Telephone Link", Digi Bio–FASEB 97, Abstract only, <http://digibio.com/cgi–bin/node.pl?lg=us&nd=n4_3>.

Aissa, et al., Molecular signaling at high dilution or by means of electronic circuitry:, Journal of Immunology, 146A, 1994, Abstract only.

Benveniste, et al., "Digital biology: Specificity of the digitized molecular signal", FASEB Journal, A412, 1997, Abstract only, <http://digibio.com/cgi–bin/node.pl?lg=us&nd=n4_2>.

Benveniste, et al., "Digital Recording/Transmission of the Cholinergic Signal", DigiBio—FASEB 96, Abstract only, <http://digibio.com/cgi–bin/node.pl?lg=us&nd=n4_4>.

Benveniste et al., "Specific Remote Detection of Bacteria Using an Electromagnetic/Digital Procedure", FASEB Journal, vol. 13, p. A852, 1999, Abstract only, <http://digibio.com/cgi–bin/node.pl?lg=us&nd=4_12>.

Benveniste et al., "The Molecular Signal is not Functional in the Absence of "Informed" Water", FASEB Journal, vol. 13, p. A163, 1999, Abstract only, <http://digibio.com/cgi–bin/node.pl?lg=us&nd=n4_11>.

Benveniste et al., "A Simple and Fast Method for in Vivo Demonstration of Electromagnetic Molecular Signaling (EMS) via High Dilution or Computer Recording", FASEB Journal, vol. 13, p. A163, 1999, Abstract only.

Benveniste et al., "Digital Biology: Specificity of the Digitized Molecular Signal", FASEB Journal, vol. 12, p. A412, 1998, Abstract only.

Benveniste, et al., "Electronic transmission of the cholinergic signal", FASEB Journal, A683, 1995, Abstract only.

Benveniste, et al., "Transfer of molecular signals via electronic circuitry", FASEB Journal, A602, 1993, Abstract only.

Benveniste, J., et al., "Transfer of the molecular signal by electronic amplification", FASEB Journal, A398, 1994, Abstract only.

Benveniste, J., "Molecular Signaling, What Is So Unacceptable for Ultra–Orthodox Scientists?", 2 pages, <http://www.digibio.com/cgi–bin/node.pl?nd=n5>.

Benveniste, J., "From 'Water Memory' effects to 'Digital Biology'. . . —Understanding Digital Biology", 4 pages <http://www.digibio.com/cgi–bin/node.pl?nd=n3>, Jun. 14, 1998.

Binhi, V., "An Analytical Survey of Theoretical Studies in the Area of Magnetoreception", 11 pages, <http://www.biomag.info/survey.htm>, 1999.

Brault, J., et al., "The Analysis and Restoration of Astronomical Data via the Fast Fourier Transform", Astronomy and Astrophysics, vol. 13, No. 2, Jul. 1971, pp 169–189.

Brigham, E., "The Fast Fourier Transform and Applications", Prentice–Hall, 1988, pp 131–145.

DigiBio S.A., Experimental models, From "Water Memory" effects to "Digital Biology", <http://digibio.com/cgi–bin/node.pl?nd=n7>.

"Direct Nanoscale Conversion of Bio–Molecular Signals Into Electronic Information" DARPA Defense Sciences Office, 2 pages, <<http://www.darpa.mil/dso/thrust/biosci/moldice.htm>>.

"Engineered Bio–Molecular Nano–Devices/Systems (MOLDICE)" DARPA Defense Sciences Office, 1 page, <<http://www.darpa.mil/dso/thrust/biosci/moldice.htm>>.

Chapeau–Blondeau, F., "Input–output gains for signal in noise in stochastic resonance", Physics Letters A, vol. 232, pp. 41–48, Jul. 21, 1997, Elsevier Science B.V.

Chapeau–Blondeau, F., "Periodic and Aperiodic Stochastic Resonance with Output Signal–to–Noise Ratio Exceeding That At The Input", International Journal of Bifurcation and Chaos, vol. 9, No. 1, pp. 267–272, 1999, World Scientific Publishing Company.

Duhamel, P., et al., "'Split radix' FFT algorithm", Electronics Letters, The Institution of Electrical Engineers, vol. 20, No. 1, Jan. 5, 1984, pp. 14–16.

Glanz, J., "Sharpening the Senses with Neural 'Noise'", Science, vol. 277, No. 5333, Sep. 19, 1997, 2 pages, http://complex.gmu.edu/neural/papers/others/science97_noise.html.

Gorgun, S., "Studies on the Interaction Between Electromagnetic Fields and Living Matter Neoplastic Cellular Culture.", 22 pages, <http://bodyvibes.com/study1.htm>.

Hoffman, F., "An Introduction to Fourier Theory", 10 pages, <http://aurora.phys.utk.edu/~forrest/papers/fourier/index.html>.

Kaufman, I. et al., "Zero–dispersion stochastic resonance in a model for a superconducting quantum interference device", Physical Review E, vol. 57, No. 1, pp. 78–87, Jan. 1998, The American Physical Society.

Nokazi, D., et al., "Effects of Colored Noise on Stochastic Resonance in Sensory Neurons", Physical Review Letters, The American Physical Society, vol. 82, No. 11, Mar. 15, 1999, 4 pages.

Oppenheim, et al., "Digital Signal Processing", Prentice–Hall, 1975, ISBN 0–13–214635–5, pp 87–121.

Proakis, J.G., et al., "Advanced digital signal processing", Maxwell MacMillan, 1992, pp 31–57.

Soma, R., "Noise Outperforms White Noise in Sensitizing Baroreflex Function in the Human Brain", Physical Review Letters, vol. 91, No. 7, 4 pages, Aug. 15, 2003, The American Physical Society.

"The First International Workshop on TFF; What is Biophysies Behind?", Abstract Booklet, Jun. 15, 1996, 18 pages, <http://www.biophysics.nl/idras.htm>.

Thomas, Y., et al., "Activation of human neurophils by electronically transmitted phorbol–myristate acetate", Medical Hypotheses, vol. 54, No. 1, pp 33–39.

Thomas, et al., "Direct transmission to cells of a molecular signal via an electronic device", FASEB Journal, A227, 1995, Abstract only.

Thomas, et al., "Modulation of Human Neutrophil Activation by "Electronic" Phorbol Myristate Acetate (PMA)", DigiBio, Abstract only, <http://www.digibio.com/cgi–bin/node.pl?lg=us&nd=n4_5.

Turin, L., "A spectroscopic mechanism for primary olfactory reception", Chemical Senses, vol. 21, No. 6, pp. 773–791.

Weaver, J., et al., "The response of living cells to very weak electrip fields: the thermal noise limit.", National Library of Medicine, 2 pages, Mar. 2, 1990, <http://www.ncbi.nlm.nih.gov/entrez/query.fcgi?db=PubMed&cmd=Retrieve&list_uids=2300806&dopt=Citation>.

* cited by examiner

SYSTEM AND METHOD FOR SAMPLE DETECTION BASED ON LOW-FREQUENCY SPECTRAL COMPONENTS

CROSS-REFERENCE TO RELATED APPLICATION(S)

This application is a continuation of International Application No. PCT/US03/11834 filed Apr. 18, 2003 and claims priority to U.S. Provisional Patent Application Nos. 60/374,941, filed Apr. 19, 2002; 60/374,043, filed Apr. 19, 2002; and 60/433,361, filed Dec. 12, 2002, all of which are incorporated herein in their entireties by reference.

REFERENCES

U.S. Pat. Nos. 4,751,515, 5,734,353, 5,952,978, 5,959,548, 6,028,558, 6,204,821, 6,323,632.
Introduction to Digital Signal Processing, Proakis and Manolakis, (Macmillan, 1988, ISBN 0-02-396810-9).
Advanced Digital Signal Processing, Proakis, Rader, Ling and Nikias, (Macmillan, 1992, ISBN 0-02-396841-9).
The Fast Fourier Transform and Its Applications, Brigham, E. Oren, (Prentice-Hall, Inc., 1988).
The Fourier Transform and Its Applications, Bracewell, Ron N., (McGraw-Hill Book Company, 1965).
The analysis and restoration of astronomical data via the fast Fourier transform, Brault, J. W. and White, O. R., 1971, Astronomy & Astrophysics., 13, pp. 169–189.
Split-radix FFT Algorithm, Duhamel, P. and Hollmann, H., 1984, Electr. Letters, vol. 1, pp. 14–16, January.
An algorithm for the machine calculation of complex Fourier series, Cooley, J. W. and Tukey, J. W., 1965, Mathematics of Computation, 19, 90, pp. 297–301.
Digital Signal Processing, Oppenheim, Alan & Schafer, Ronald, (1975, ISBN 0-13-214635-5).
An Introduction to Fourier Theory, by Forrest Hoffman, ("http://aurora.phys.utk.edu/~forrest/papers/fourier/index.html#introduction").

BACKGROUND

There are a variety of spectroscopic tools for characterizing atomic or molecular compound. These include, but are not limited to, x-ray, UV, visible-light, infrared and microwave spectroscopy, and nuclear and electron spin resonance (NMR and ESR) spectroscopy. In general, spectroscopic tools are useful for at least four different type of chemical-analytical problems: first, to characterize an atomic and molecular compound according to its spectrographic features, e.g., spectral components; second, to determine the atomic composition of a compound, according to the spectral characteristics of atoms making up the compound; third, to determine 2-D or 3-D conformation of a molecular compound according to the spectral characteristic of atom-atom interactions in the compound; and fourth, to detect and identify components, e.g., contaminants, in a sample according to the distinguishing spectral characteristics of the compound being detected.

Most existing spectroscopic tools provide some unique advantage(s) in terms of sensitivity, the information gained, ease of measurement and cost. Because each tool provides information not otherwise available, it is generally advantageous to be able to bring to bear on any chemical-analytical, as many pertinent spectroscopic tools as possible.

SUMMARY

In one aspect, the invention includes an apparatus for use in detecting a selected material in a sample or environment(s). A data storage device in the apparatus stores, for each of one or more preselected materials including the selected material, a data set containing low-frequency spectral components that are (i) in a selected frequency range between dc to 50 Khz, and (ii) characteristic of that material. A detector assembly in the apparatus has a detector coil for generating a time-domain signal having signal components related to low-frequency electromagnetic radiation produced by the selected material in the sample, when the sample is placed adjacent the coil. Signal conditioning components in the apparatus convert the signal from the detector coil to an amplified conditioned signal from which frequency components above a selected frequency have been removed.

An electronic computer in the apparatus receives the conditioned signal and processes this signal by the steps of
(i) retrieving from the data storage device (a), a data set of low-frequency spectral components characteristic of the selected sample material,
(ii) filtering the conditioned signal, with such in digitized form, to selectively pass low-frequency spectral components corresponding to those of the retrieved data set;
(iii) cross-correlating the filtered signal from (ii) with the data set of low-frequency spectral components from (i) to produce a frequency-domain spectrum in a frequency range within dc to 50 khz, and
(iv) determining whether the frequency-domain spectrum contains one or more low-frequency signal components that are characteristic of the selected material, and diagnostic of the presence or absence of such material in the sample.

The output of the processing steps may be stored or displayed on an interface device connected to the computer.

For use in detecting a material in a fluid sample, the detector assembly may include a sample tube having sample inlet and outlet ports through which sample can be directed through the tube. The detector coil may be wound about the tube in a winding direction substantially perpendicular to the direction of sample flow in the tube. The tube is preferably formed of pyrex glass or other material that is transparent to low-frequency electromagnetic signals, but itself produces little or no low-frequency signal. The detector assembly may further include a toroidal ferrite core having the collector tube disposed about at least a portion of the circumference of the core, with the detector coil wound around the tube and core in a radial winding direction. Also in this general embodiment, the detector assembly may further include a source of Gaussian noise and a noise-injection coil wound about the circumference of the toroidal core, through which Gaussian noise can be introduced from the source into the sample in the tube.

In another general embodiment, the detector coil in the detector assembly includes a Helmholz coil having a pair of opposed coil elements between which the sample can be placed. In one embodiment, the opposed coil elements define an open sample-detection region therebetween, through which self-supporting samples can be inserted and removed.

In still another embodiment, the detector coil is a Tesla coil.

For use in detecting gaseous or particulate material in a gaseous-stream sample, the detector assembly includes a filter effective to trap sample material, as the sample passes through the filter. The detector coil is placed against the filter with its winding direction substantially parallel to the filter.

The computer may be operable, in carrying out processing step (iv), to identify the frequencies of low-frequency signal components in the spectrum whose cross-spectral correlations have a selected statistical measure above background spectral noise.

The computer may be operable, in carrying out step (iv), to (iva) receive an additional frequency-domain spectrum for a given sample, (ivb) add the additional spectrum to the originally produced spectrum, and average the added spectra, and (ivc) repeat steps (iva) and (ivb) until components in the summed and averaged spectrum have a selected statistical measure above background noise.

In another aspect, the invention includes a method for detecting a selected material in a sample. In practicing the method, a sample is placed adjacent a detector coil, thereby to generate an electromagnetic time-domain signal composed of sample source radiation. The signal is converted to an amplified conditioned signal from which frequency components above a selected frequency have been removed, then filtered to selectively pass low-frequency spectral components that are (i) in a frequency range between dc and 50 kHz, and (ii) characteristic of the selected material.

The filtered signal is cross-correlated with a data set of low-frequency spectral components that are (i) in a frequency range between dc and 50 kHz, and (ii) characteristic of a selected material, to produce a frequency-domain spectrum in the frequency range within DC to 50 kHz. By determining whether the frequency-domain spectrum contains one or more low-frequency signal components that are characteristic of the selected material, the presence or absence of such material in the sample is detected.

For use in detecting a material in a fluid sample, the sample may be flowed through a sample tube having sample inlet and outlet ports. Here the detector coil may be wound about the tube in a winding direction substantially perpendicular to the direction of sample flow in the tube. The sample tube may be disposed adjacent a toroidal ferrite core, with the detector coil wound around the tube and core in a radial winding direction. In this embodiment, the method may further include injecting Gaussian noise into the sample during generation of the time-domain signal.

Alternatively, the detector coil may be a Helmholz coil having a pair of opposed coil elements. In this embodiment, the sample may be placed between the coil elements.

For use in detecting gaseous or particulate material in a gaseous-stream sample, the sample may be passed sample through a filter effective to trap sample material, as the sample passes through the filter. The detector coil is placed adjacent the filter, preferably with a winding direction substantially parallel to the plane of the filter.

The step of determining whether the frequency-domain spectrum contains one or more low-frequency signal components that are characteristic of the selected material may include identifying the frequencies of low-frequency signal components in the spectrum whose cross-spectral correlations have a selected statistical measure above background spectral noise.

The step of determining whether the frequency-domain spectrum contains one or more low-frequency signal components that are characteristic of the selected material may include (a) receiving an additional frequency-domain spectrum for a given sample, (b) adding the additional spectrum to the originally produced spectrum, and averaging the added spectra, and (c) repeating steps (a) and (b) until components in the summed and averaged spectrum have a selected statistical measure above background noise.

These and other aspects and features of the invention will become more fully apparent when the following detailed description of embodiments the invention is read in conjunction with the accompanying drawings.

DETAILED DESCRIPTION

I. Definitions

The terms below have the following definitions unless indicated otherwise.

"Sample that exhibits molecular rotation" refers to a sample material, which may be in gaseous, liquid or solid form (other than a solid metal) in which one or more of the molecular compounds or atomic ions making up or present in the sample exhibit rotation.

"Time-domain signal" or "time-series signal" refers to a signal with transient signal properties that change over time.

"Sample-source radiation" refers to magnetic flux emissions resulting form the rotation of a molecular dipole in a magnetic field.

"Gaussian noise" means random noise having a Gaussian power distribution.

"Stationary white Gaussian noise" means random Gaussian noise that has no predictable components "Frequency-domain spectrum" refers to a Fourier frequency plot of a time-domain signal.

"Spectral components" refer to singular or repeating qualities within a time-domain signal that can be measured in the frequency, amplitude, and/or phase domains. Spectral components will typically refer to signals present in the frequency domain.

"Similar sample," with reference to a first sample, refers to the same sample or a sample having substantially the same sample components as the first sample.

II. Apparatus

The apparatus of the invention operates at the extreme low end of the electromagnetic spectrum between Direct Current (DC) and 50 Kilohertz. (KhZ) This technology is passive, which means it does not require 'painting' the target with harmful, or ionizing radiation (although some embodiments inject white noise into the system/sample). In at least one embodiment, this molecular sensing invention detects naturally occurring thermal electromagnetic radiation and offers a fast, simple method for remotely sensing extremely small molecular concentrations. Applications include, but are not limited to: remote sensing of weapons, explosives and biohazards, detection of genetically modified grains and crops, real-time detection of organisms such as *E. coli* and the aids virus, and real-time chemical analysis of process streams in volatile, corrosive or thermal environments.

This remote sensing system detects molecular electromagnetic emissions, performs time series Fourier spectral analysis and compares the results against archived data, identifying molecular materials in near real time that may not be otherwise detectable. The device has the ability to detect multiple materials simultaneously and is scalable from small handheld devices to large industrial applications.

Figure 1:
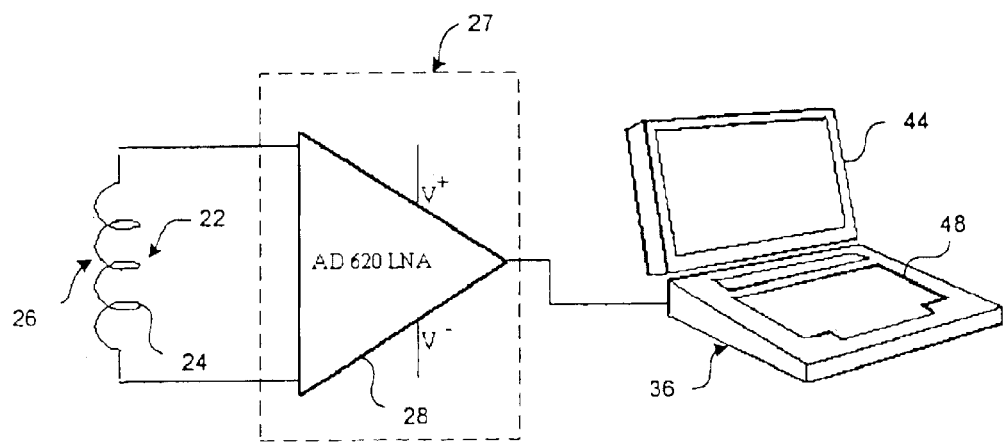
FIG. 1 shows components of an apparatus constructed in accordance with one embodiment of the invention.
Figure 6A:
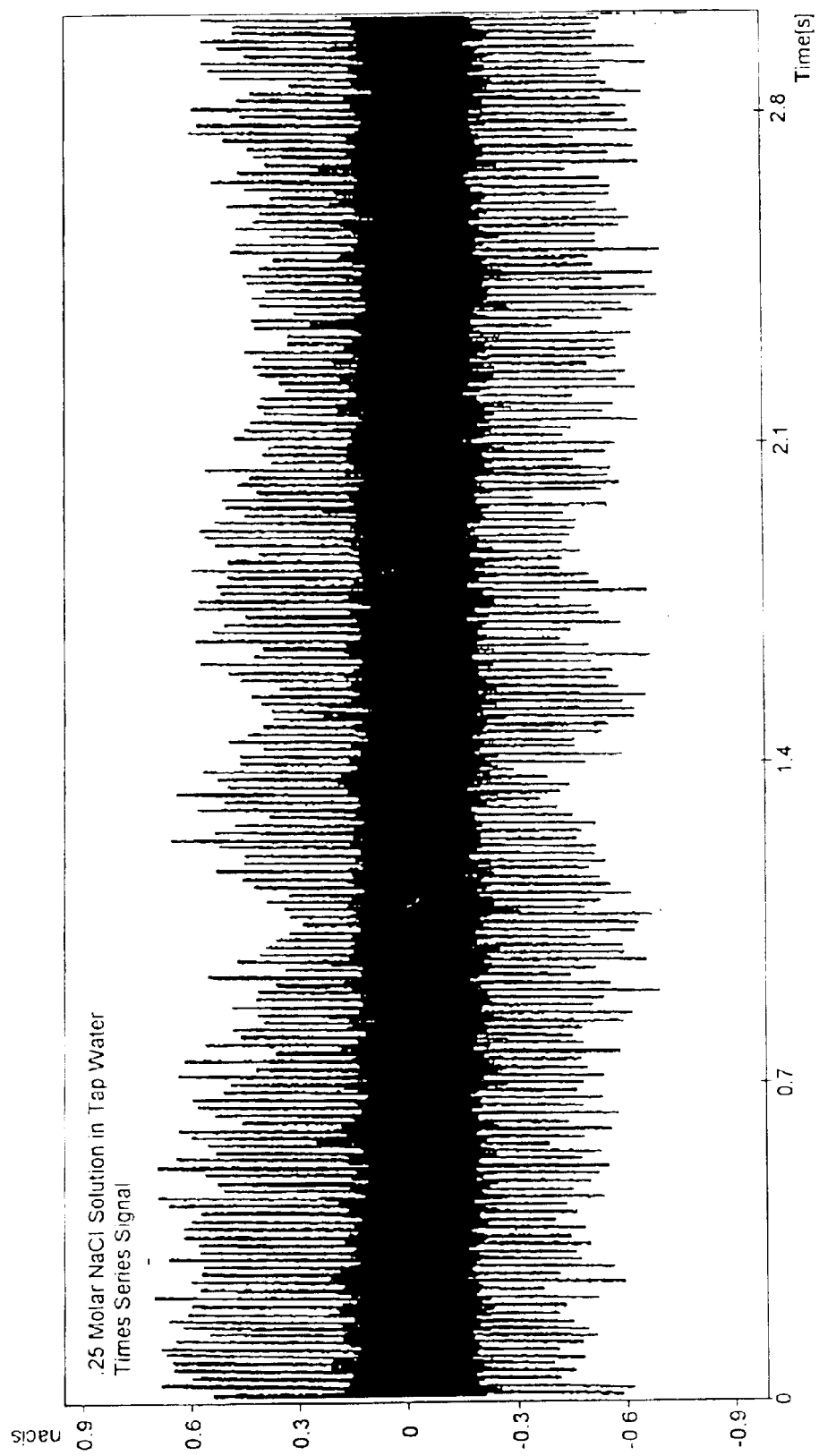
FIG. 6A shows a time-domain signal recorded from an NaCl solution, in accordance the method of the invention.

FIG. 1 illustrates an apparatus 20 constructed according to one embodiment of the invention, for detecting a selected material, e.g., compound, ionic species, particulate material, contained in a sample. The apparatus include a detector assembly 22 having a detector coil 24 for generating a time-domain signal related to low-frequency electromagnetic radiation produced by the material in the sample. Although not shown in FIG. 1, the sample is placed in a sample region 26 adjacent the coil. As will be seen below, the sample region may include an open region between sample coils, a sample collector, such as a membrane, or a sample tube through which sample material can be flowed. The sample region, including specific sample holders, is also considered part of the detector assembly. FIG. 6A shows a typical time-domain signal for a 0.25 M NaCl sample recorded with the apparatus of the invention.

Figure 3:
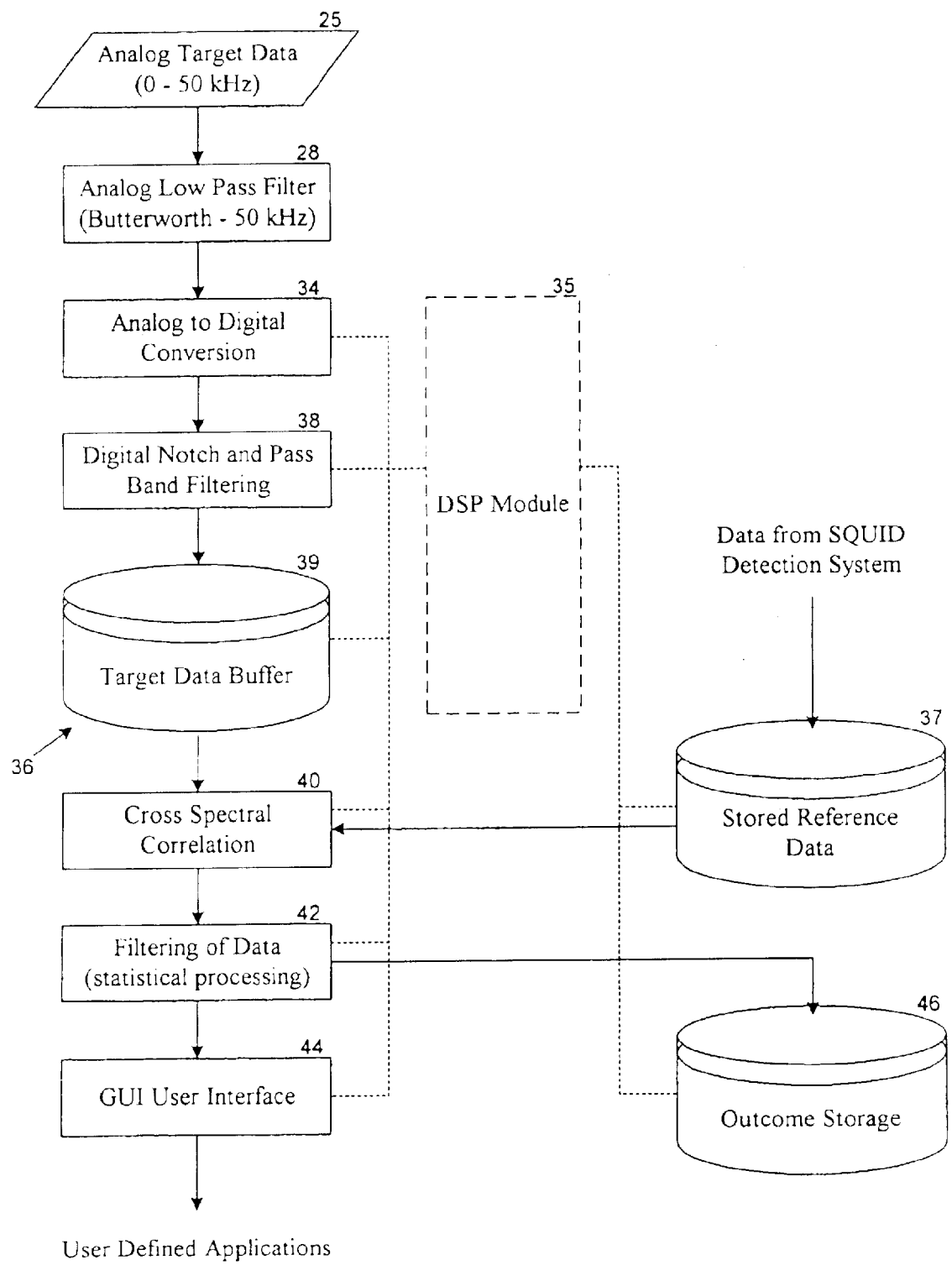
FIG. 3 is a block diagram of signal processing for streaming data
Figure 6B:
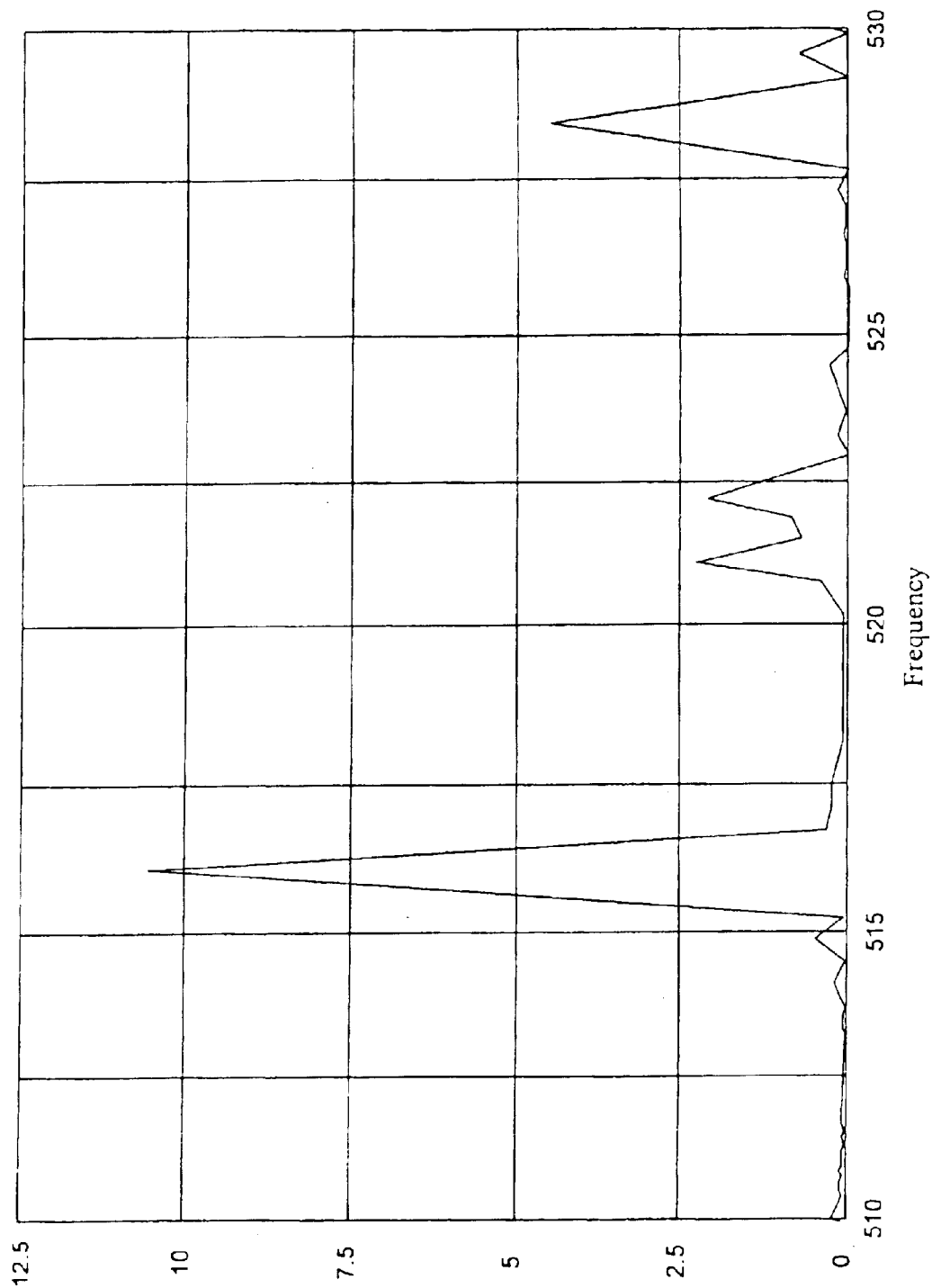
FIG. 6B shows the time-domain signal from FIG. 6A after signal amplification and removal of higher-frequency components.
Figure 6C:
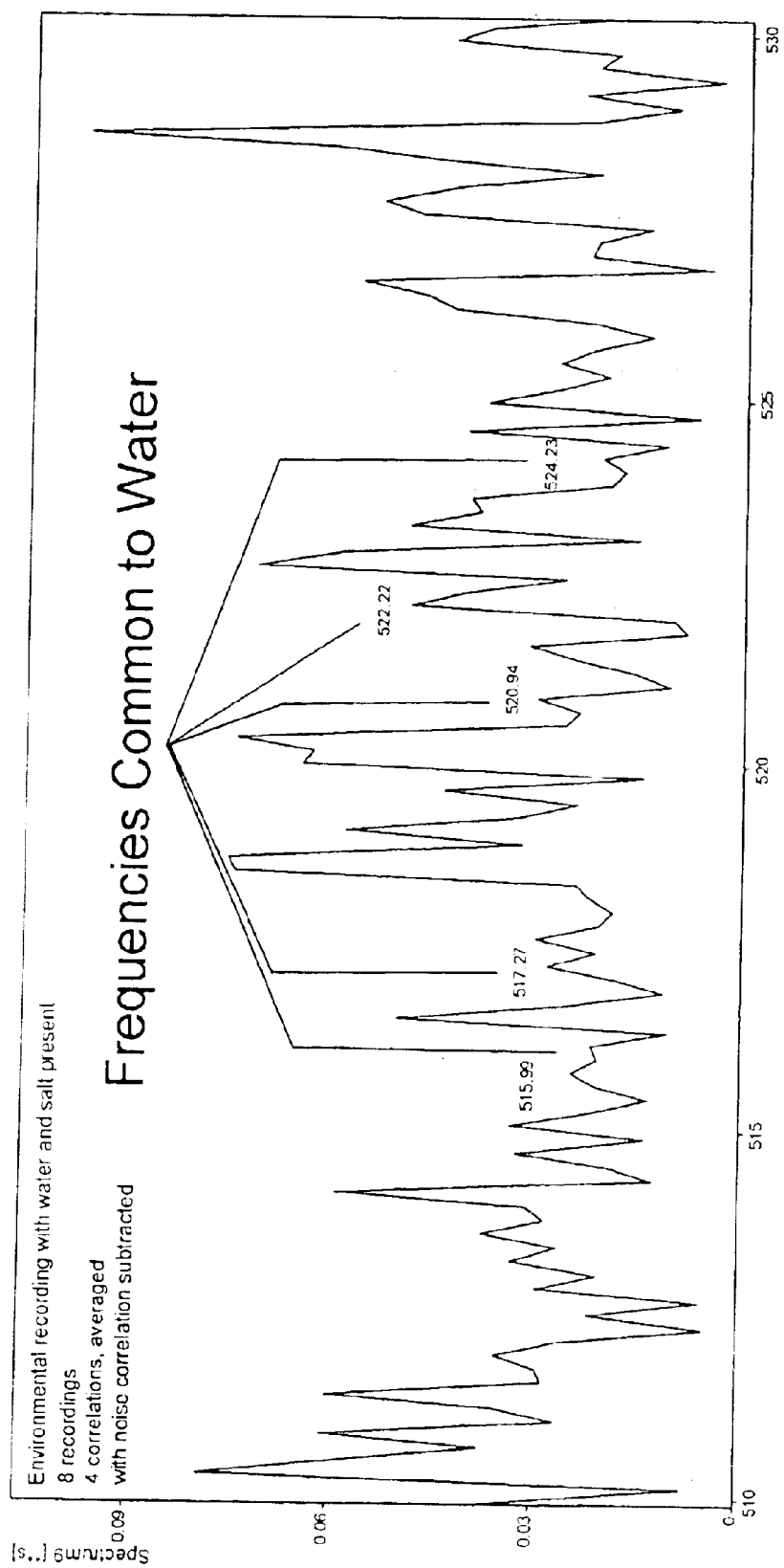
FIG. 6C shows the time-domain signal from FIG. 6B after notch filtering to pass selected low-frequency spectral components of a solution of NaCl.

Shown at 27 are signal conditioning components for converting the signal from the detector coil to an amplified conditioned signal from which frequency components above a selected frequency have been removed. These components, which are illustrated in FIG. 3, which also shows at 25 the target analog signal generated by the detector assembly. Components 27 in the figure include a low-noise amplifier 28 (an AD 620 LNA 7 or equivalent is suitable) that amplifies the signal to a serviceable level, e.g., with a gain of 1 to 1000. The amplifier's gain is addressable by the user as a method for adjusting the sensitivity the sensing device. Also include in components 27 is an analog low-pass filter which functions to condition the signal for A/D conversion by passing frequencies below 50 kHz, such as a conventional Butterworth analog filter. This filter adjusts and limits the bandwidth of the received signal depending on down stream processing requirements. This filter is addressable by the user and by the interpreter, depending on data characteristics held in archive. If the primary spectral components of an archived signal occur within a narrow bandwidth the interpreter can instruct the filter to narrow the bandwidth, thereby increasing the efficiency of the Fourier processor. The digital filter also may provide a notch filter to remove unwanted signals in noisy environments. FIG. 6B shows the FIG. 6A signal for a 0.25 M NaCl sample after amplification and band-pass filtering to remove frequency components above 50 kHz.

The output of the low-pass filter is supplied to an analog-to-digital converter 34 for converting the amplified filtered analog signal to digital form. A typical A/D converter is 16 bit analog to digital converter, such as supplied Analog Devices (Los Angeles, Calif.), although other resolutions are possible, such as 24 bit.

The output of the A/D converter is operably connected to an electronic computer 36 in the apparatus for performing a series of signal processing steps leading to the identification of spectral components that are diagnostic of the sample material to be identified, as will be described. The computer includes a digital signal processing module 35 which designed for high speed signal processing operations as will be described. Also included in the computer is a data-storage device 37, such as a conventional thin-film storage device 37 for storing, for each of one or more preselected materials including the selected material, a data set containing low-frequency spectral components that are (i) in a selected frequency range between DC to 50 khz, and (ii) characteristic of that material. This data set is generated by recording and processing low-frequency signals from a selected material under conditions of high magnetic and electromagnetic shielding, using the low-frequency recording device described in PCT Application No. PCT/US03/09544, filed Mar. 28, 2003, for "System and Method for Characterizing a Sample by Low-Frequency Spectra," which is incorporated by reference herein. Further details are provided below in the section "Generating Signals".

Briefly, the low-frequency recording device produces a data set containing a plurality of low-frequency spectral components, typically in the range 100 Hz to 6.6 kHz, but including the broader range of dc to 50 kHz, that are characteristic of the sample material, e.g., water, an ionized salt, a solute material, a undesired contaminant, a biological sample material or the like. In general, the more complex the sample material, the more complex (the greater the number of characteristic spectral components) the sample material data set will contain. As will be appreciated from below, the ability to detect a selected sample material by the method of the present invention relies on the fact that different selected materials of interest are characterized by different spectral "signatures," that is, different sets of characteristic low-frequency components, such that at least one, and typically several of the characteristic spectral components of a material will be unique to that material.

The nature of the data sets that are installed on the storage device in the apparatus will depend on the selected materials one wishes to detect with the apparatus. Typically, for a mobile field unit, the data sets will include data sets for all material one expects to detect in a filed setting, include, for example, various contaminants that may be present in a water sample, or various air-borne sample one may wish to detect, such as atmospheric particulates, air-borne biological particles or chemical components present in the air.

As indicated above, the computer is designed to perform a variety of signal processing operations, as indicated in FIG. 3. The first operation signal processing is carried out to selectively pass frequency components corresponding to the low-frequency spectral components of the sample material of interest. Thus, this stage performs the function of a plurality of notch filters, each notch passing one of the spectral bands in the data set for the material of interest. In performing this operation, the computer first retrieves from the data storage device, a data set of low-frequency spectral components characteristic of the selected sample material, and records the low-frequency spectral components associated with that material. This data is used in a conventional digital notch and band pass filter 38 to (i) remove (notch filter) 60 Hz frequency components, and pass those frequencies (band pass filter) corresponding to spectral frequencies in the retrieved data set. In general, the digital filter passes selected frequencies between direct current and 50 kHz. The pass band filter may consist of an array of addressable digital filters capable of providing multiple pass bands while also providing a notch filter at power line frequencies and other known noise frequencies. The digital filter is addressable by the processor and may also be configured to be user addressable.

There may be some compression in the A/D conversion of signals. There is also a data buffer 39 between the ADC and the Fourier processor for temporarily storing streaming data from the input. The results of the analysis (not the signal) will be presented in some form of graphic display and will also be stored in the onboard data archive for later retrieval.

In the next processing step, the band-pass filtered time-domain signal is cross-correlated at 40 with the spectral components of the retrieved data set, to generate a frequency-domain spectrum in a frequency range within DC to 50 KHz that contains, as spectral components, those spectral frequencies present in both the filtered signal and the data set. That is, the spectrum will evidence, by the presence of absence of characteristic spectral components, the presence of absence of the sample material of interest. The cross-correlation module performs a time series Fast Fourier Transform on the received data using radix-2, radix-4, or a split-radix algorithm. The resulting data is representative of the original signal consisting of spectral amplitudes measured in seconds per cycle (time series equivalent to Time, Frequency, and Amplitude). A spectrum for 0.25 M NaCl generated by cross-correlating the FIG. 6B signal with a data set of spectral components for this sample is shown in 6C.

The cross-correlation function may be performed by a monolithic processor chip programmed to perform a Fourier correlative analysis of the unknown signal compared with Fourier data from a known signal. The results of the analysis will be rendered as a percentage spectral fit between the unknown signal and the known signal. The 'fit' percentage will correlate to statistical significance and this data is then sent on to an interpreter to be filtered through an algorithm to determine the likelihood of a positive detection or match.

The processor may be a digital signal processor ("DSP") or a microprocessor instructed to perform cross spectral correlations against archived data. The processor may act independently, or in conjunction with other processors, depending on architecture. This processor may also provide instruction to the active digital filters to establish Fourier filters as signal preparation for cross spectral correlation. The processor may be part of a larger processing system which includes data storage and an appropriate user interface with output device(s) (e.g. visual display, speakers for audio, wireless transceiver, etc.). The user interface may provide for user control over the amplifier and filter modules, ADC and correlator.

Typically, the spectrum generated above will require additional filtering, and/or summing and averaging operations to enhance the spectral components and/or evaluate whether the spectral components are above a defined statistical threshold that permits a reliable measure of identification of the selected sample material. In one exemplary method, a cross-correlated sample signal spectrum is compared with a cross-correlated noise (no sample) signal. A comparator algorithm the advances incrementally, e.g., in 0.1 Hz intervals across the cross-correlated sample spectrum and the cross-correlated noise spectrum, looking at the correlation value at each frequency point, and subtracts the noise correlation from the sample correlation at that point, to yield a frequency plot of corrected correlation values. (Of course, greater or lesser frequency intervals may be used depending upon the application.) These values will be relative to a particular sample, and depend, for example, on the relative amplitude of any noise component.

Figure 6D:
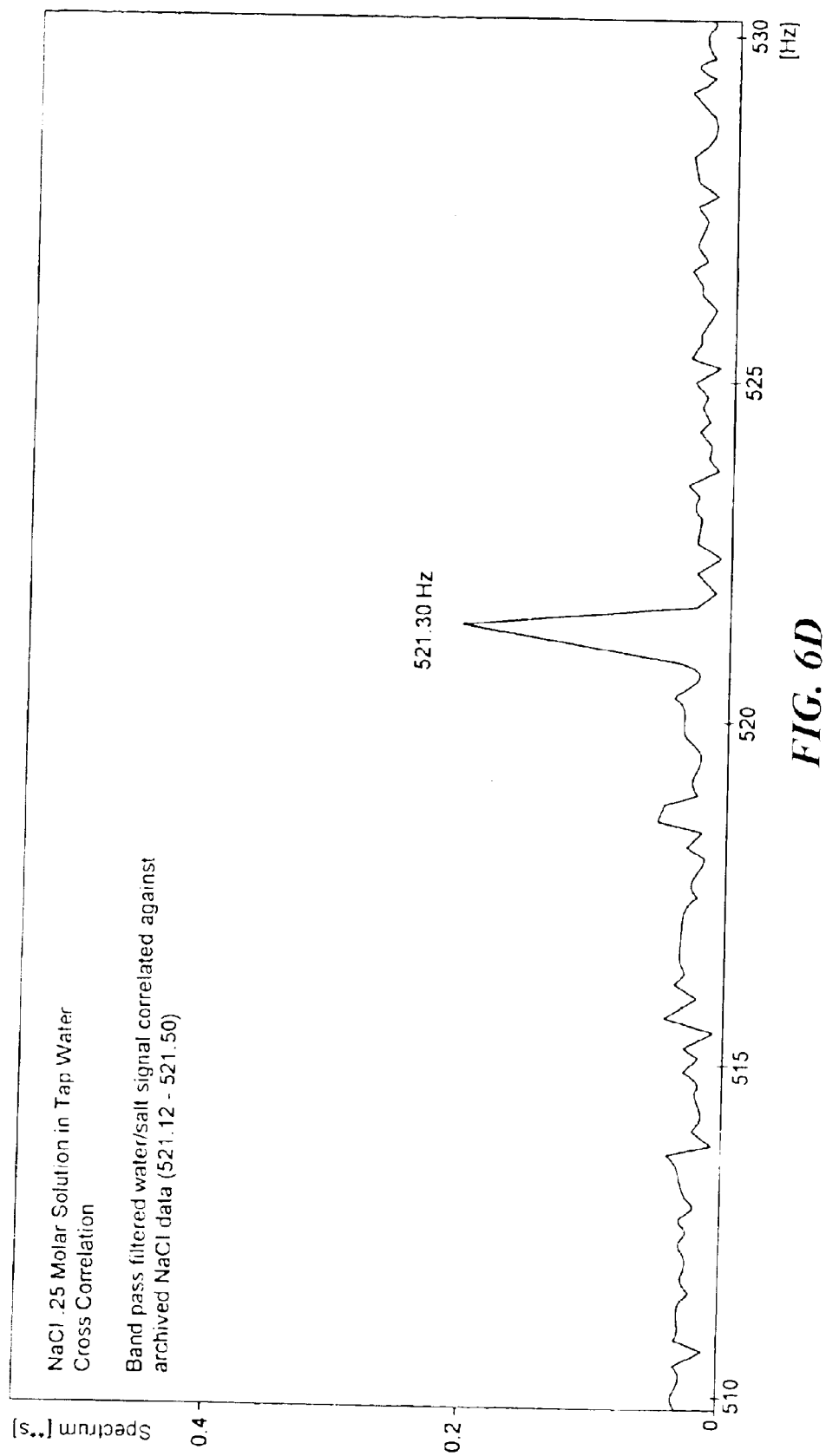
FIG. 6D shows a frequency-domain spectrum of NaCl produced by cross-correlating the filtered signal from 6C with a data set of low-frequency spectral components associated with NaCl; showing a low-frequency spectral component characteristic of NaCl.

Alternatively, the spectrum generated from a single reading may be summed and averaged successively with spectra produced from the same sample. That is, a second spectrum produced as above from the same sample is added to the first spectrum, and the two spectrum and summed and averaged. This process is repeated until spectral components above a statistical threshold are observed. These components are then "read" or compared to determine if they match the characteristic frequencies of the selected material. The above operations are carried out as shown at 42 in FIG. 3. A summed and averaged spectrum for an NaCl sample is shown in FIG. 6D.

The interpreter may be another monolithic processor chip capable of storing and using a simple algorithm to determine an outcome from an event (or may be a routine performed by the above processor chip or system components). The event will be a number reflecting the statistical significance (as a percentage) of the fit between the unknown and known signals. The algorithm will measure the 'fit' against preset thresholds to determine the likelihood of a match based on the known characteristics of the spectral data for a specific molecule. As an example, one molecule may have exceptionally high spectral energy within certain frequencies and cycles over time. Another molecule may have more uniform spectral energy over those same frequencies and time. Each of these molecules may be produce a statistical significance that is different but of equal weight. The interpreter compensates for this when there are multiple known molecular datasets in data archive. In its simplest embodiment, the interpreter is a threshold against which the percentage fit signal is compared. The threshold may be adjusted based on various factors (e.g. reduce the threshold if the environmental noise level is high).

The data and/or results of the determinations are shown to the user at a computer display 44. Alternatively, or in addition, the results are stored in a storage device 46, typically one associated with the computer. Also as shown in FIG. 1, the computer has a keyboard 48 by which the user can specify signal processing parameters, sample identification, and so forth.

A typical output will identify the selected sample of interest, and display a table with side-by-side columns listing (i) the spectral components associated with the selected sample, and (ii) those statistically meaningful sample components that match those from the data set. From this, the user will be able to determine whether the selected material is in the sample. The output may also show an averaged spectrum from which the spectral components are derived, to provide the user with some statistical measure of the reliability of the results.

Figure 2:
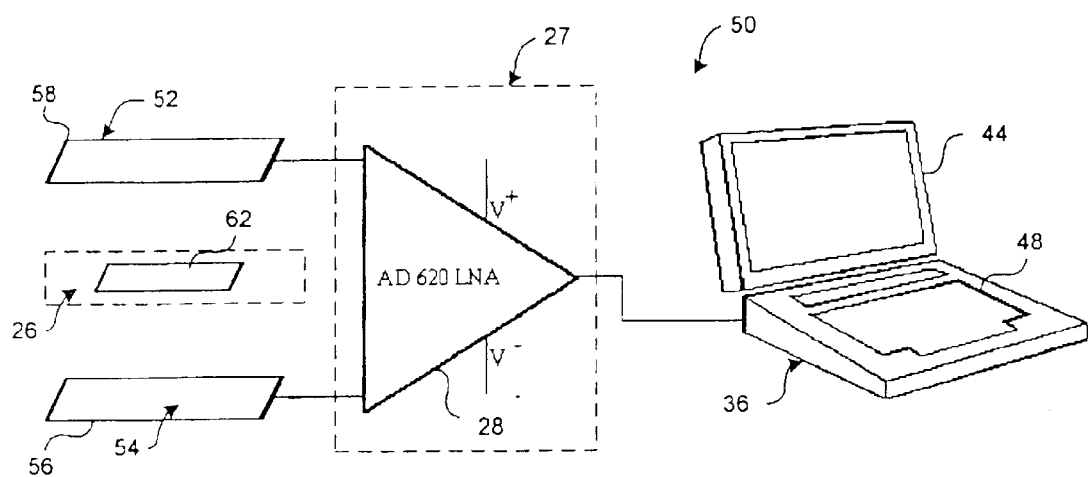
FIG. 2 shows components of an apparatus constructed in accordance with another embodiment of the invention.

An apparatus 50 constructed according to a second embodiment of the invention is illustrated in FIG. 2. The apparatus here differs from apparatus 20 just described in the detector assembly only, and thus other components of the apparatus are shown by the same reference numerals as indicated from apparatus 20. The detector assembly in the apparatus, indicated at 52, includes as the detector coil, a Helmholz coil 54 comprised of a pair of opposing coil elements 56, 58. The two coils elements define a sample region 60 between the elements through which a sample, such as indicated at 62, can be moved. This embodiment is useful, for example, for detecting samples, such as portable objects, that are being screened or checked. As shown, the coil elements are separately connected to the signal amplifier in the noise injection coils. In operation, the two separate signals are processed the same as above.

Numerous alternative components are possible. For example, while the detector coil is a tuned coil designed to operate between direct current and 50 kHz capable of detecting low frequency electromagnetic emissions present in a specific area, a variety of coils can be implemented including, but not limited to: Tesla coils, toroidal coils, Helmholtz coils, slug tuned coils, and measured wavelength and random wire loops.

The next two sections describe alternative detector assemblies, the first having a sample tube and a toroidal detector for detecting material in a fluid sample, and the second having a filter sample collector for detecting a gas-borne sample material.

A. Toroidal Detector

Many commercial and industrial applications require materials to be evaluated in a process stream in noisy electromagnetic environments. Sensing molecular material inside a toroidal transformer provides a high level of electromagnetic isolation. Applications for this system include, but are not limited to, real-time chemical analysis of process streams in volatile, corrosive or thermal environments, testing air for contaminates in commercial or public environments, and testing water supplies or other commercially available consumables.

The system provides the ability to move fluids and gasses through a toroidal transformer while using the fluid or gas as a replacement for the primary emitting element. A gas or fluid is pumped around the circumference of the toroid between the torus core and induction coil. Gaussian white noise is injected inside the toroid via a noise element wrapped in a 1:1 ratio with a sample tube that moves the gas or liquid through the toroid (although other ratios may be used).

As molecular material moves through the toroid, Gaussian white noise is injected 30 to 35 dBs above the level of the molecular signal. The molecular signal sums with the white noise to form a stochastic product that retains identifying characteristics of the molecular signal. The signal is then amplified and processed as described above, to identify material in the sample having a unique low-frequency spectral signature.

The device uses the folded magnetic field of a toroid and provides inductance between the primary and secondary element (sample tube and detection coil). The confined magnetic field (B) inside the toroid cavity is accurately quantified by the simple equation: $B=A/r$, where A is a proportionality constant (torus factor), and r is the radial distance from the long axis of the cavity.

Figure 4:
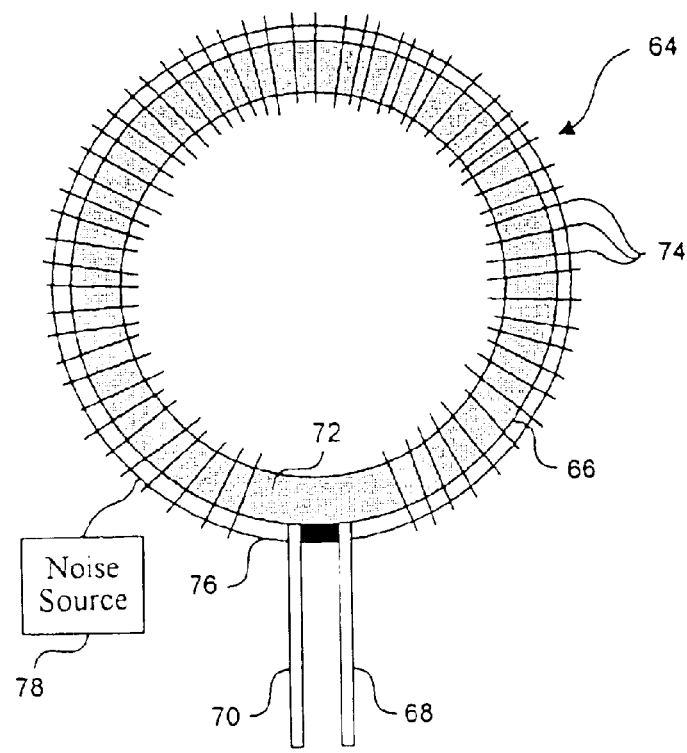
FIG. 4 shows elements of a toroidal detector assembly constructed in accordance with one embodiment of the invention.

A toroidal detector assembly constructed in accordance with this embodiment of the invention is shown in plan view at 64 in FIG. 4. A glass, plastic, preferably Pyrex tube 66 is disposed about the outer circumference of a toroidal core 72 formed of a ferromagnetic material, such as Ferrite. The tube communicates at its opposite ends with inlet and outlet ports 68, 70, respectively, allowing liquid or gas samples to be pumped through the tube during a detection operation. The dimensions of the toroid and tubing are dependent on the individual application and are only critical to the end-product design specifications. Further, the tube ring could be positioned in other locations within the coil, such as within a center of the core 72.

A noise injection coil 76 is disposed about the outer circumference of the tube, as indicated. While the coil 76 is shown as one loop, it could take the form of coils disposed as the windings 74. The purpose of coil 76 is to allow the addition of Gaussian noise supplied from a Gaussian noise source noise 78 into the sample.

A secondary winding 74 which forms the detector coil in the assembly is wrapped radially around the toroid core, tube 66, and noise coil 76. The size and type of the wire and the number of turns around the toroid is dependent on the resonant frequency of the secondary coil. Although not critical, the configuration should be such as to achieve as high a Q factor as possible for the transformer. The detector coil is connected to a signal amplifier for signal conditioning as described above.

In operation, a fluid or a gas is pumped through the transformer in such a manner as to provide a sustained low velocity flow. Sample material transiting through the tubing emit extremely low amplitude electromagnetic waves that are detected by the coil. White noise is injected into the area of the sample via a noise coil so as to mix with the natural electromagnetic emission from the target material. Gain is then applied to the noise until the noise is 30 to 35 dbs above the target signal. At this point the noise takes on the characteristics of the underlying signal, effectively amplifying the molecular signal under a natural condition known as stochastic resonance. The stochastic product creates an induced voltage in the secondary coil that is picked up and amplified by a preamplifier circuit.

The system effectively uses ambient electromagnetic environmental noise as a stochastic source and applying Fourier analysis to identify stochastic (waveform) features that resemble (waveform) features of specific molecules. This also establishes theoretical limits on the functional range of the detector.

Note, the scale of the toriod is dependent upon the application. For example, a very large detector may be created with a large toroid to thereby sample a large volume of material.

B. Air Detector

Figure 5:
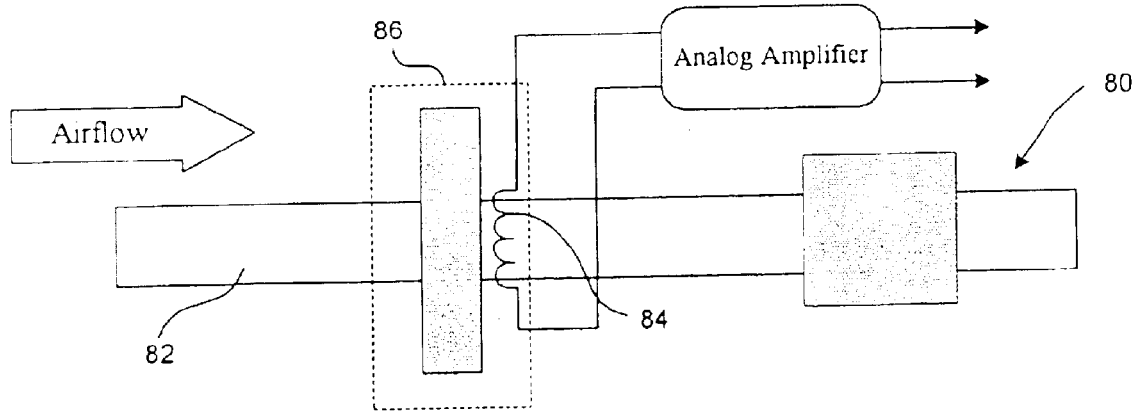
FIG. 5 shows elements of a collector assembly for airborne material constructed in accordance with another embodiment of the invention.

Illustrated in FIG. 5 is apparatus 80 having an air-sample detector assembly intended for the detection and identification of an unknown materials entrained in a gaseous form, e.g., air-borne particles. The assembly includes an air transport tube, e.g., a 1 micron particulate filter, a detection coil 84, a radio frequency shield 86, and a pump 88 for pumping air through the tube and through the filter. The detector coil is oriented with its windings parallel to the plane of the filter, and placed directly against the back surface of the filter The air tube can be made of any suitable material, although plastics and fiber composite materials may be preferable. The purpose of the air tube is to allow airborne particulates to move through the device. A removable 1 micron electrostatic filter is used to trap airborne particulates as air moves through the filter. Alternatively, where the apparatus is intended to measure material in molecular gas form, such as NO, $SO_2$, fluorocholorohydrocarbons, alkyl gases, and the like, the filter may provide a chemically reactive surface on which the material may be adsorbed or absorbed, or with which the material may react.

Where it is necessary to dissolve the selected material of interest in a solvent in order to detect its low-frequency rotational modes, the detector assembly in the apparatus may alternatively include separate collector and detection stations. Thus, for example, the apparatus may include a system for collecting material on a filter, and a separate detection system that includes a reservoir of solvent in which the filter is placed, allowing trapped material on the filter to release into the solvent, e.g., water or organic solvent. The solution of suspended material may then be interrogated with the solution in a Pyrex vessel having a detector-coil winding about the outside of the vessel.

In still another embodiment, the air is drawn through a reservoir of solvent, e.g., water or an organic solvent in which the molecular-gas material is dissolved. That is, the air sample is bubbled through the reservoir at a rate effective to trap the selected material of interest. In this embodiment, the detector coil may be wound about the exterior of the reservoir, e.g., the exterior of a Pyrex cylindrical vessel through which the air is bubbled. The liquid sample with entrapped gas material may also be transferred to a separate detector, e.g., the above toroidal detector described above.

III. Generating Signals

Details on how certain signals, such as baseline or data set signals used for comparing with sampled signals will now be described.

Figure 7:
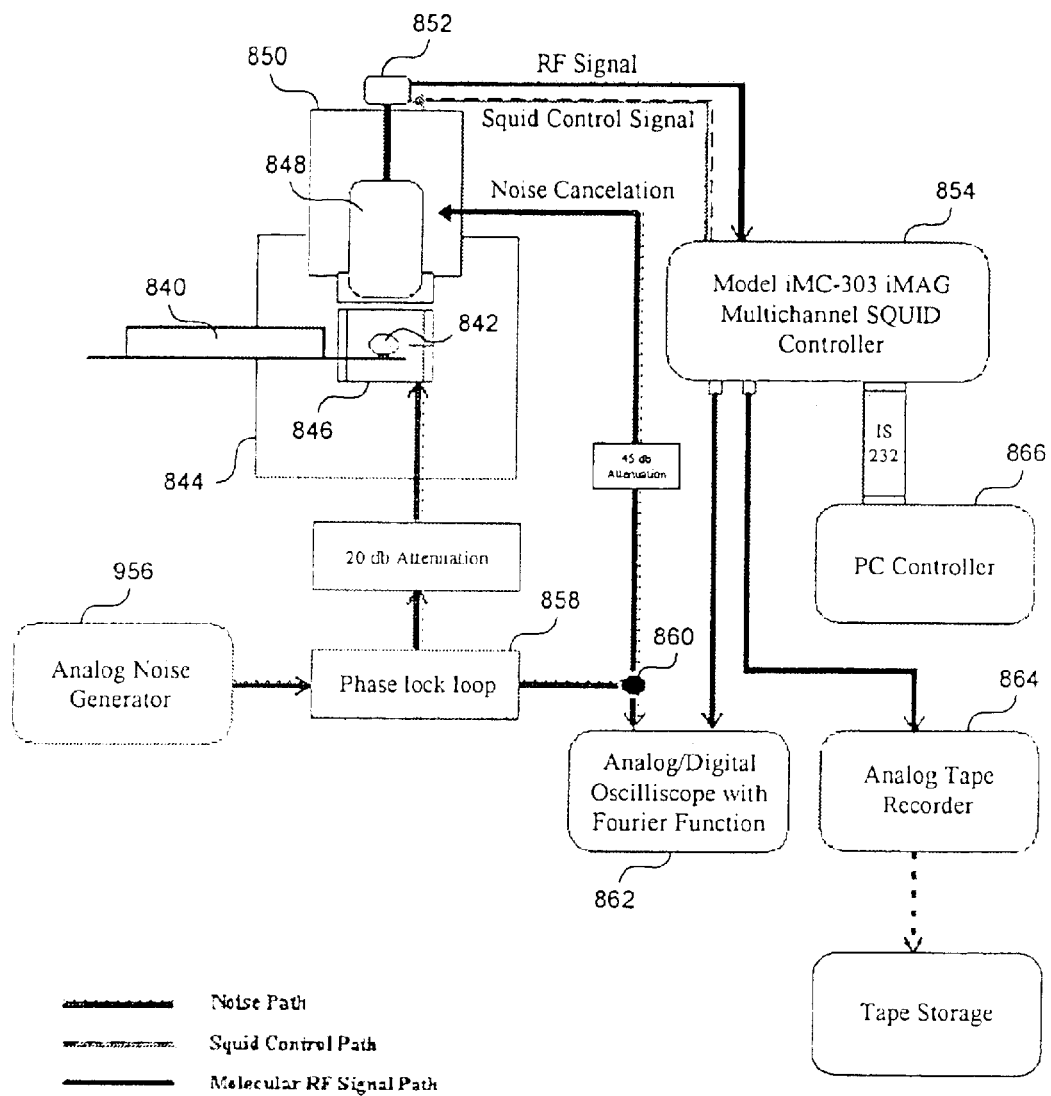
FIG. 7 is a diagram of the processing unit included in the detection system.

Referring to FIG. 7, a processing unit employing aspects of the invention includes a sample tray 840 that permits a sample 842 to be inserted into, and removed from, a Faraday cage 844 and Helmholtz coil 846. A SQUID/gradiometer detector assembly 848 is positioned within a cryogenic dewar 850. A flux-locked loop 852 is coupled between the SQUID/gradiometer detector assembly 848 and a SQUID controller 854. The SQUID controller 854 may be a model iMC-303 iMAG multichannel controller provided by Tristan of San Diego.

An analog noise generator 856 provides a noise signal (as noted above) to a phase lock loop 858. The x-axis output of the phase lock loop is provided to the Helmholtz coil 846, and may be attenuated, such as by 20 dB. The y-axis output of the phase lock loop is split by a signal splitter 860. One portion of the y-axis output is input the noise cancellation coil at the SQUID, which has a separate input for the gradiometer. The other portion of the y-axis signal is input oscilloscope 862, such as an analog/digital oscilloscope having Fourier functions like the Tektronix TDS 3000b. That is, the x-axis output of the phase lock loop drives the Helmholz coil, and the y-axis output, which is in inverted form, is split to input the SQUID and the oscilloscope. Thus, the phase lock loop functions as a signal inverter. The oscilloscope trace is used to monitor the analog noise signal, for example, for determining when a sufficient level of noise for producing non-stationary spectral components is achieved. An analog tape recorder or recording device 864, coupled to the controller 854, records signals output from the device, and is preferably a wideband (e.g. 50 kHz) recorder. A PC controller 866 may be an MS Windows based PC interfacing with the controller 854 via, for example, an RS 232 port.

Figure 8:
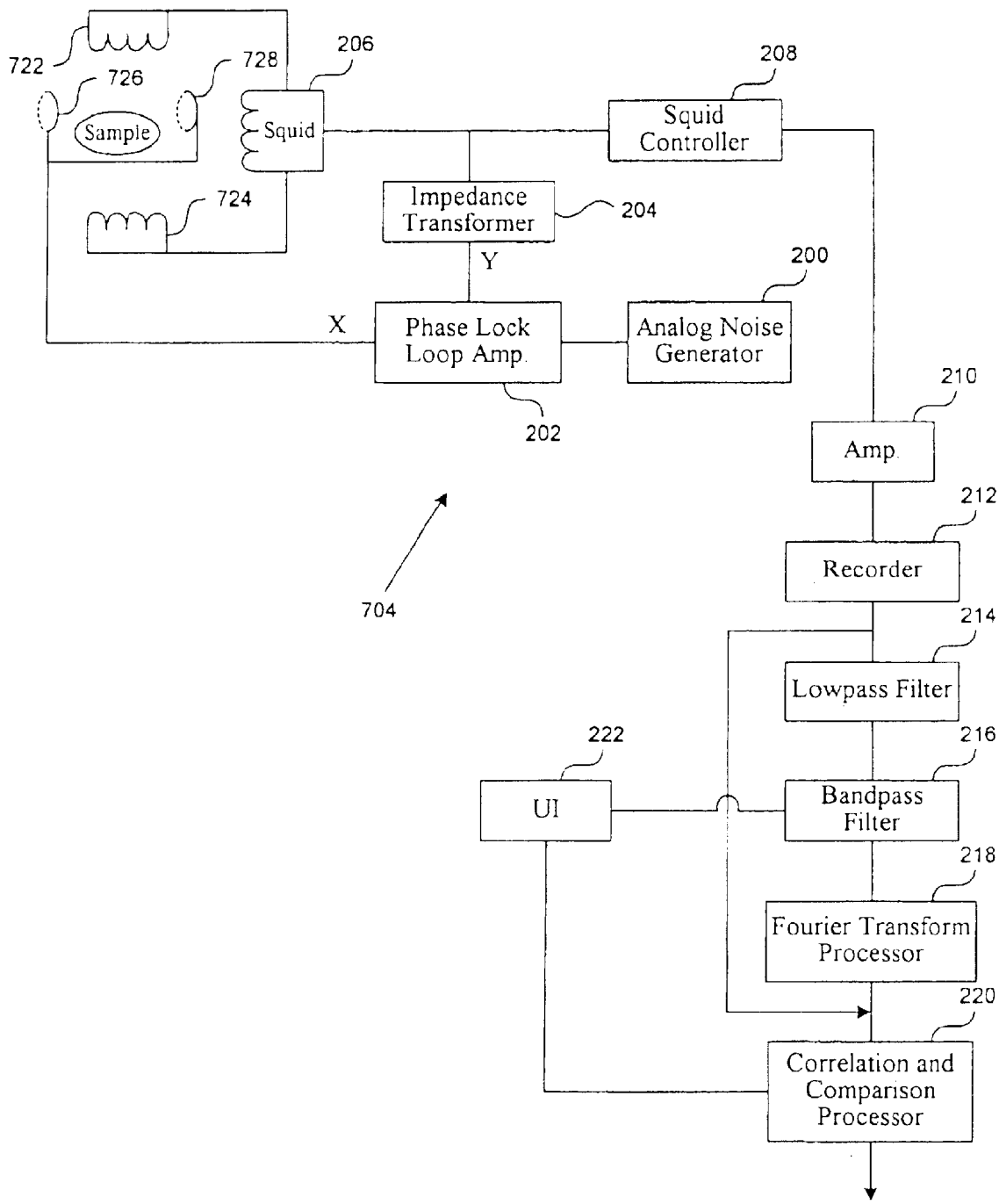
FIG. 8 is a diagram of an alternative processing unit of that of FIG. 7.

In FIG. 8, a block diagram of another embodiment of the processing unit is shown. A dual phase lock-in amplifier 202 is configured to provide a first signal (e.g., "x" or noise signal) to coils 726, 728 and a second signal (e.g., "y" or noise cancellation signal) to a noise cancellation coil of a superconducting quantum interference device (SQUID) 206. The amplifier 202 is configured to lock without an external reference and may be a Perkins Elmer model 7265 DSP lock-in amplifier. This amplifier works in a "virtual mode," where it locks to an initial reference frequency, and then removes the reference frequency to allow it to run freely and lock to "noise."

An analog noise generator 200 is electrically coupled to the amplifier 202. The generator 200 is configured to generate or induce an analog white Gaussian noise at the coils 726, 728 via the amplifier 202. As an example, the generator 200 may be a model 1380 manufactured by General Radio.

An impedance transformer 204 is electrically coupled between the SQUID 206 and the amplifier 202. The impedance transformer 204 is configured to provide impedance matching between the SQUID 206 and amplifier 202.

The noise cancellation feature of the SQUID 206 can be turned on or off. When the noise cancellation feature is turned on, the SQUID 206 is capable of canceling or nullifying the injected noise component from the detected emissions. To provide the noise cancellation, the first signal to the coils 726, 728 is a noise signal at 20 dB above the molecular electromagnetic emissions sought to be detected. At this level, the injected noise takes on the characteristics of the molecular electromagnetic signal through stochastic resonance. The second signal to the SQUID 206 is a noise cancellation signal at 45 dB and is inverted from the first signal at an amplitude sufficient to null the noise at the SQUID output (e.g., 180 degrees out of phase with respect to the first signal).

The SQUID 206 is a low temperature direct element SQUID. As an example, the SQUID 206 may be a model LSQ/20 LTS dC SQUID manufactured by Tristan Technologies, Inc. Alternatively, a high temperature or alternating current SQUID can be used. Coils 722, 724 (e.g., gradiometer coils) and the SQUID 206 (collectively referred to as the SQUID/gradiometer detector assembly) combined has a magnetic field measuring sensitivity of approximately 5 microTesla/√Hz. The induced voltage in the coils 722, 724 is detected and amplified by the SQUID 206. The output of the SQUID 206 is a voltage approximately in the range of 0.2–0.8 microVolts.

The output of the SQUID 206 is the input to a SQUID controller 208. The SQUID controller 208 is configured to control the operational state of the SQUID 206 and further condition the detected signal. As an example, the SQUID controller 208 may be an iMC-303 iMAG multi-channel SQUID controller manufactured by Tristan Technologies, Inc. A flux-locked loop may be operatively positioned between the SQUID and the SQUID controller.

The output of the SQUID controller 208 is inputted to an amplifier 210. The amplifier 210 is configured to provide a gain in the range of 0–100 dB. A gain of approximately 20 dB is provided when noise cancellation node is turned on at the SQUID 206. A gain of approximately 50 dB is provided when the SQUID 206 is providing no noise cancellation.

The amplified signal is inputted to a recorder or storage device 212. The recorder 212 is configured to convert the analog amplified signal to a digital signal and store the digital signal. In one embodiment, the recorder 212 stores 8600 data points per Hz and can handle 2.46 Mbits/sec. As an example, the recorder 212 may be a Sony digital audio tape (DAT) recorder. Using a DAT recorder, the raw signals or data sets can be sent to a third party for display or specific processing as desired. A lowpass filter 214 filters the digitized data set from the recorder 212. The lowpass filter 214 is an analog filter and may be a Butterworth filter. The cutoff frequency is at approximately 50 kHz.

A bandpass filter 216 next filters the filtered data sets. The bandpass filter 216 is configured to be a digital filter with a bandwidth between DC to 50 kHz. The bandpass filter 216 can be adjusted for different bandwidths.

The output of the bandpass filter 216 is the input to a Fourier transformer processor 218. The Fourier transform processor 218 is configured to convert the data set, which is in the time domain, to a data set in the frequency domain. The Fourier transform processor 218 performs a Fast Fourier Transform (FFT) type of transform.

The Fourier transformed data sets are the input to a correlation and comparison processor 220. The output of the recorder 212 is also an input to the processor 220. The processor 220 is configured to correlate the data set with previously recorded data sets, determine thresholds, and perform noise cancellation (when no noise cancellation is provided by the SQUID 206). The output of the processor 220 is a final data set representative of the spectrum of the sample's molecular low frequency electromagnetic emissions.

A user interface (UI) 222, such as a graphical user interface (GUI), may also be connected to at least the filter 216 and the processor 220 to specify signal processing parameters. The filter 216, processor 218, and the processor 220 can be implemented as hardware, software, or firmware. For example, the filter 216 and the processor 218 may be implemented in one or more semiconductor chips. The processor 220 may be software implemented in a computing device.

This amplifier works in a "virtual mode," where it locks to an initial reference frequency, and then removes the reference frequency to allow it to run freely and lock to "noise." The analog noise generator (which is produced by General Radio, a truly analog noise generator) requires 20 dB and 45-dB attenuation for the Helmholz and noise cancellation coil, respectively.

The Helmholz coil may have a sweet spot of about one cubic inch with a balance of $1/100^{th}$ of a percent. In an alternative embodiments, the Helmholtz coil may move both vertically, rotationally (about the vertical access), and from a parallel to spread apart in a pie shape. In one embodiment, the SQUID, gradiometer, and driving transformer (controller) have values of 1.8, 1.5 and 0.3 micro-Henrys, respectively. The Helmholtz coil may have a sensitivity of 0.5 Gauss per amp at the sweet spot.

Approximately 10 to 15 microvolts may be needed for a stochastic response. By injecting noise, the system has raised the sensitivity of the SQUID device. The SQUID device had a sensitivity of about 5 femtotesla without the noise. This system has been able to improve the sensitivity by 25 to 35 dB by injecting noise and using this stochastic resonance response, which amounts to nearly a 1,500% increase.

After receiving and recording signals from the system, a computer, such as a mainframe computer, supercomputer or high-performance computer does both pre and post processing, such by employing the Autosignal software product by Systat Software of Richmond Calif., for the pre-processing, while Flexpro software product does the post-processing. Flexpro is a data (statistical) analysis software supplied by Dewetron, Inc.

Figure 9:
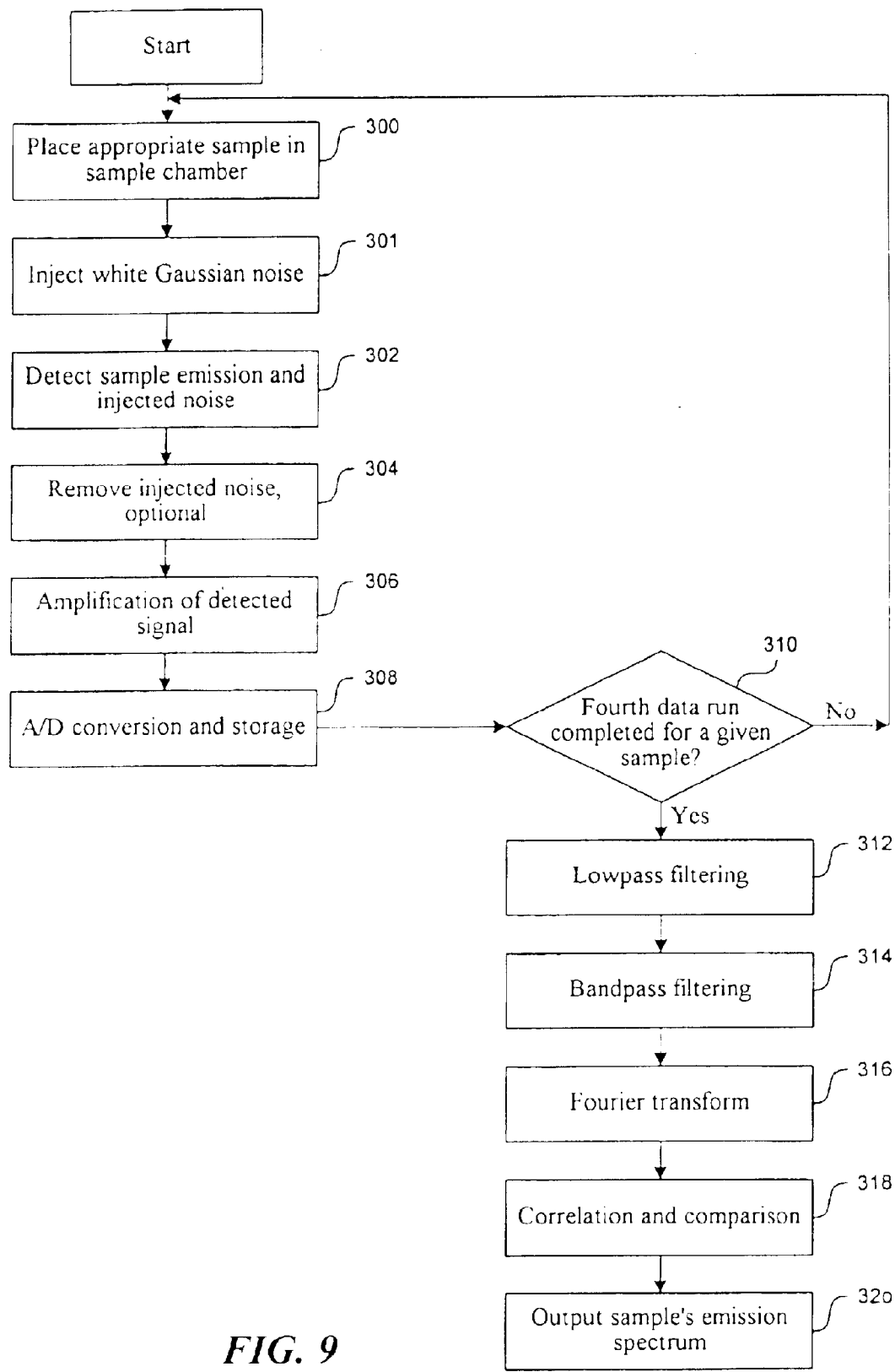
FIG. 9 is a flow diagram of the signal detection and processing performed by the present system.

A flow diagram of the signal detection and processing performed by the system is shown in FIG. 9. When a sample is of interest, at least four signal detections or data runs may be performed: a first data run at a time $t_1$ without the sample, a second data run at a time $t_2$ with the sample, a third data run at a time $t_3$ with the sample, and a fourth data run at a time $t_4$ without the sample. Performing and collecting data sets from more than one data run increases accuracy of the final (e.g., correlated) data set. In the four data runs, the parameters and conditions of the system are held constant (e.g., temperature, amount of amplification, position of the coils, the noise signal, etc.).

At a block 300, the appropriate sample (or if it's a first or fourth data run, no sample), is placed in the system. A given sample, without injected noise, emits electromagnetic emissions in the DC-50 kHz range at an amplitude equal to or less than approximately 0.001 microTesla. To capture such low emissions, a white Gaussian noise is injected at a block 301.

At a block 302, the coils 722, 724 detect the induced voltage representative of the sample's emission and the injected noise. The induced voltage comprises a continuous stream of voltage values (amplitude and phase) as a function of time for the duration of a data run. A data run can be 2–20 minutes in length and hence, the data set corresponding to the data run comprises 2–20 minutes of voltage values as a function of time.

At a block 304, the injected noise is cancelled as the induced voltage is being detected. This block is omitted when the noise cancellation feature of the SQUID 206 is turned off.

At a block 306, the voltage values of the data set are amplified by 20–50 dB, depending on whether noise cancellation occurred at the block 304. And at a block 308, the amplified data set undergoes analog to digital (A/D) conversion and is stored in the recorder 212. A digitized data set can comprise millions of rows of data.

After the acquired data set is stored, at a block 310 a check is performed to see whether at least four data runs for the sample have occurred (e.g., have acquired at least four data sets). If four data sets for a given sample have been obtained, then lowpass filtering occurs at a block 312. Otherwise, the next data run is initiated (return to the block 300).

After lowpass filtering (block 312) and bandpass filtering (at a block 314) the digitized data sets, the data sets are converted to the frequency domain at a Fourier transform block 316.

Next, at a block 318, like data sets are correlated with each other at each data point. For example, the first data set corresponding to the first data run (e.g., a baseline or ambient noise data run) and the fourth data set corresponding to the fourth data run (e.g., another noise data run) are correlated to each other. If the amplitude value of the first data set at a given frequency is the same as the amplitude value of the fourth data set at that given frequency, then the correlation value or number for that given frequency would be 1.0. Alternatively, the range of correlation values may be set at between 0–100. Such correlation or comparison also occurs for the second and third data runs (e.g., the sample data runs). Because the acquired data sets are stored, they can be accessed at a later time as the remaining data runs are completed.

When the SQUID 206 provides no noise cancellation, then predetermined threshold levels are applied to each correlated data set to eliminate statistically irrelevant correlation values. A variety of threshold values may be used, depending on the length of the data runs (the longer the data runs, greater the accuracy of the acquired data) and the likely similarity of the sample's actual emission spectrum to other types of samples. In addition to the threshold levels, the correlations are averaged. Use of thresholds and averaging correlation results in the injected noise component becoming very small in the resulting correlated data set.

If noise cancellation is provided at the SQUID 206, then the use of thresholds and averaging correlations are not necessary.

Once the two sample data sets have been refined to a correlated sample data set and the two noise data sets have been refined to a correlated noise data set, the correlated noise data set is subtracted from the correlated sample data set. The resulting data set is the final data set (e.g., a data set representative of the emission spectrum of the sample) (block 320).

Since there can be 8600 data points per Hz and the final data set can have data points for a frequency range of DC-50 kHz, the final data set can comprise several hundred million rows of data. Each row of data can include the frequency, amplitude, phase, and a correlation value.

IV. Methods and Applications

This section describes the method of the invention for interrogating detecting one or more selected materials in liquid or gaseous sample. In practicing the method, a sample containing a selected material of interest is placed adjacent a detector coil, e.g., in one of the detector assemblies noted above. The detector coil then converts low-frequency electromagnetic emissions in the material, due at least in part to rotational modes of the material, to an electromagnetic time-domain signal composed of sample source radiation.

The signal is conditioned to convert it to an amplified conditioned signal from which frequency components above a selected frequency have been removed. The filtered, conditioned time-domain signal to selectively pass low-frequency spectral components that are (i) in a frequency range between dc and 50 khz, and (ii) characteristic of the selected material. This is done by retrieving a data set of spectral components that are characteristic of that material, and filtering the conditioned signal to selectively pass, e.g., with a band width of 0.5 to 1 Hz, one of more of the frequency components characteristic of the material.

The filtered signal is now cross-correlated with a data set of low-frequency spectral components that are (i) in a frequency range between dc and 50 khz, and (ii) characteristic of a selected material, to produce a frequency-domain spectrum in the frequency range within dc to 50 khz. From this spectrum, it is determined whether the frequency-domain spectrum contains one or more low-frequency signal components that are characteristic of the selected material, and diagnostic of the presence or absence of such material in the sample.

Applications of the method for detecting air, water, food, cosmetic, and industrial samples are noted above, as are applications in screening luggage or airline passengers for harmful or illegal substances.

From the foregoing, it will be appreciated how various objects and features of the invention are met. The method and apparatus do not require activation of sample and do not employ x-radiation or other potentially destructive radiation. The invention is applicable to a wide range of materials, with the only requirement that the material be in any environment that allows molecular rotational movement. Further, the sample being tested can be liquid or air, or a person or a persons' effects, for screening purposes.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while processes or steps are presented in a given order, alternative embodiments may perform routines having steps in a different order. While these steps are shown in a particular order, in some embodiments these steps are re-arranged, and some steps may be deleted, moved, added, subdivided, combined, and/or modified. Each of these steps may be implemented in a variety of different ways. Also, while these steps are shown as being performed in series, these steps may instead be performed in parallel, or may be performed at different times.

The teachings of the invention provided herein can be applied to other systems, not necessarily the system described herein. These and other changes can be made to the invention in light of the detailed description. The elements and acts of the various embodiments described above can be combined to provide further embodiments.

All of the above U.S. patents and applications and other references are incorporated herein by reference. Aspects of the invention can be modified, if necessary, to employ the systems, functions and concepts of the various references described above to provide yet further embodiments of the invention.

These and other changes can be made to the invention in light of the above detailed description. In general, the terms used in the following claims should not be construed to limit the invention to the specific embodiments disclosed in the specification, unless the above detailed description explicitly defines such terms. Accordingly, the actual scope of the invention encompasses not only the disclosed embodiments, but all equivalent ways of practicing or implementing the invention under the claims.

While certain aspects of the invention are presented below in certain claim forms, the inventors contemplate the various aspects of the invention in any number of claim forms. For example, while only one aspect of the invention is recited as embodied as a method, other aspects may likewise be embodied as a method. Accordingly, the inventors reserve the right to add additional claims after filing the application to pursue such additional claim forms for other aspects of the invention.

It is claimed:

1. Apparatus for use in detecting a selected material in a sample, comprising (a) a sample holder for holding the sample, the holder being shielded from ambient electrical and magnetic energy, (b) a noise generator for introducing noise into the sample, without ionizing the sample, (c) a data storage device for storing, for each of one or more preselected materials including the selected material, a data set containing low-frequency spectral components that are (i) in a selected frequency range between DC to 50 kHz, and (ii) characteristic of that material, (d) a detector assembly including a detector coil adjacent the sample holder for producing a time-domain signal having signal components related to low-frequency electromagnetic radiation produced by the selected material in the sample, (e) signal conditioning components for converting the signal from the detector coil to an amplified conditioned signal from which frequency components above a selected frequency have been removed, (f) an electronic computer operably connected to the conditioning components to receive the conditioned signal therefrom, and for processing this signal by:
  (i) retrieving from the data storage device a data set of low-frequency spectral components characteristic of the selected sample material,
  (ii) filtering the conditioned signal, with such in digitized form, to selectively pass low-frequency spectral components corresponding to those of the retrieved data set;
  (iii) cross-correlating the filtered signal from (ii) with the data set of low-frequency spectral components from (i) to produce a frequency-domain spectrum in a frequency range within DC to 50 kHz, and
  (iv) determining whether the frequency-domain spectrum contains one or more low-frequency signal components that are characteristic of the selected material, and diagnostic of the presence or absence of such material in the sample, and
(g) an interface device operably connected to the computer for displaying the output of the processing.

2. The apparatus of claim 1, for use in detecting a material in a fluid sample, wherein the assembly includes a sample tube having sample inlet and outlet ports through which sample can be directed through the tube, and the detector coil is wound about the tube in a winding direction substantially perpendicular to the direction of sample flow in the tube.

3. The apparatus of claim 2, wherein the tube is formed of pyrex glass.

4. The apparatus of claim 2, wherein the detector assembly further includes a toroidal ferrite core having the collector tube disposed about at least a portion of the circumference of the core, and the detector coil is wound around the tube and core in a radial winding direction.

5. The apparatus of claim 4, wherein the detector assembly further includes a source of Gaussian noise and a noise-injection coil wound about the circumference of the toroidal core, through which Gaussian noise can be introduced from the source into the sample in the tube.

6. The apparatus of claim 1, wherein the detector coil includes a Helmholz coil having a pair of opposed coil elements between which the sample can be placed.

7. The apparatus of claim 6, wherein the opposed coil elements define an open sample-detection region therebetween, through which self-supporting samples can be inserted and removed.

8. The apparatus of claim 1, wherein the detection coil includes a Tesla coil.

9. The apparatus of claim 1, for use in detecting gaseous or particulate material in a gaseous-stream sample, wherein the assembly includes a collector filter effective to trap such material, as the sample passes through the filter, and the a detector coil placed against the filter and having a winding direction substantially parallel to the filter.

10. The apparatus of claim 1, wherein the computer is operable, in carrying out (iv), of identifying the frequencies of low-frequency signal components in the spectrum whose cross-spectral correlations have a selected statistical measure above background spectral noise.

11. The apparatus of claim 1, wherein the computer is operable, in carrying out (iv), of (iva) receiving an additional frequency-domain spectrum for a given sample, (ivb) adding the additional spectrum to the originally produced spectrum, and averaging the added spectra, and (ivc) repeating (iva) and (ivb) until components in the summed and averaged spectrum have a selected statistical measure above background noise.

12. A method for detecting a selected material in a sample, comprising:
  (a) placing the sample adjacent a detector coil,
  (b) while introducing noise into the sample, and without ionizing the sample, detecting an electromagnetic time-domain signal produced in the detector coil by the sample,
  (c) conditioning the time-domain signal to convert the signal to an amplified conditioned signal from which frequency components above a selected frequency have been removed,
  (d) filtering the conditioned time-domain signal to selectively pass low-frequency spectral components that are
    (i) in a frequency range between DC and 50 kHz and
    (ii) characteristic of the selected material,
  (e) cross-correlating the filtered signal from (c) with a data set of low-frequency spectral components that are
    (i) in a frequency range between DC and 50 kHz, and
    (ii) characteristic of a selected material, to produce a frequency-domain spectrum in the frequency range within DC to 50 kHz, and
  (f) determining whether the frequency-domain spectrum contains one or more low-frequency signal components that are characteristic of the selected material, and diagnostic of the presence or absence of such material in the sample.

13. The method of claim 12, for use in detecting a material in a fluid sample, wherein the placing includes flowing the sample through a sample tube having sample inlet and outlet ports, and the detector coil is wound about the tube in a winding direction substantially perpendicular to the direction of sample flow in the tube.

14. The method of claim 13, wherein the sample tube is disposed adjacent a toroidal ferrite core, the detector coil is wound around the tube and core in a radial winding direction, and which further includes injecting Gaussian noise into the sample during generation of the time-domain signal.

15. The method of claim 12, wherein the detector coil includes a Helmholz coil having a pair of opposed coil elements, and the placing includes placing the sample between the coil elements.

16. The method of claim 12, for use in detecting gaseous or particulate material in a gaseous-stream sample, wherein the placing includes passing the sample through a planar filter effective to trap such material, as the sample passes through the filter, and the detector coil has a winding direction substantially parallel to the plane of the filter.

17. The method of claim 12, wherein the determining includes identifying the frequencies of low-frequency signal components in the spectrum whose cross-spectral correlations have a selected statistical measure above background spectral noise.

18. The method of claim 12, wherein the determining includes (a) receiving an additional frequency-domain spectrum for a given sample, (b) adding the additional spectrum to the originally produced spectrum, and averaging the added spectra, and (c) repeating (a) and (b) until components in the summed and averaged spectrum have a selected statistical measure above background noise.

19. A system for detecting a selected material in a sample, comprising:
  means for holding the sample adjacent a detector coil, thereby to generate an electromagnetic time-domain signal composed of sample source radiation, without gas chromatography or ion cyclotron resonance, means for introducing noise into the sample during the signal generation, means for conditioning the time-domain signal to convert the signal to an amplified conditioned signal from which frequency components above a selected frequency have been removed, means for filtering the conditioned time-domain signal to selectively pass low-frequency spectral components that are (i) in a frequency range between DC and 50 kHz, and (ii) characteristic of the selected material, means for cross-correlating the filtered signal with a data set of low-frequency spectral components that are (i) in a frequency range between DC and 50 kHz, and (ii) characteristic of a selected material, to produce a frequency-domain spectrum in the frequency range within DC to 50 kHz, and means for determining whether the frequency-domain spectrum contains one or more low-frequency signal components that are characteristic of the selected material, and diagnostic of the presence or absence of such material in the sample.

20. The system of claim 19, further comprising means for automatically extracting the sample from an environment surrounding the system, and wherein the sample is air or gas.

21. The system of claim 19 wherein the means for placing includes toroidal detector means for detecting an electromagnetic signal from the sample.

* * * * *